United States Patent
Chandler et al.

(10) Patent No.: US 6,610,822 B2
(45) Date of Patent: Aug. 26, 2003

(54) PURIFICATION PROCESS

(75) Inventors: Martin A. Chandler, East Brunswick, NJ (US); Kent E. Goklen, Fanwood, NJ (US); Steven S. Lee, Doylestown, PA (US); David J. Roush, Colts Neck, NJ (US)

(73) Assignee: Merck & Co., Inc., Rahway, NJ (US)

( * ) Notice: Subject to any disclaimer, the term of this patent is extended or adjusted under 35 U.S.C. 154(b) by 160 days.

(21) Appl. No.: 09/920,497

(22) Filed: Aug. 1, 2001

(65) Prior Publication Data

US 2002/0028916 A1 Mar. 7, 2002

Related U.S. Application Data

(60) Provisional application No. 60/229,903, filed on Sep. 1, 2000.

(51) Int. Cl.$^7$ .............................. C07K 1/14; C07K 7/54
(52) U.S. Cl. ....................... 530/317; 530/300; 530/322; 530/344; 530/345; 514/11
(58) Field of Search ................................. 530/317, 300, 530/322, 344, 345; 514/11

(56) References Cited

U.S. PATENT DOCUMENTS

| | | | | |
|---|---|---|---|---|
| 5,021,341 A | * | 6/1991 | Giacobbe et al. | 435/71.1 |
| 5,336,756 A | * | 8/1994 | Schwartz et al. | 530/327 |

* cited by examiner

*Primary Examiner*—Christopher S. F. Low
*Assistant Examiner*—Chih-Min Kam
(74) *Attorney, Agent, or Firm*—Valerie J. Camara; Mark R. Daniel; James M. Hunter, Jr.

(57) ABSTRACT

There is disclosed a process for purifying a natural product using a two-phase, multi-solvent system followed by vacuum concentration and back extraction. The method allows for the removal of impurities by controlling the polarity balance of a two-phase system by manipulating the proportions of the four solvents and subsequently the relative distribution of the product versus the impurities.

16 Claims, 1 Drawing Sheet

PURIFICATION PROCESS

This application claims priority of U.S. provisional patent aplication No. 60/229,903 filed Sep. 1, 2000.

BACKGROUND OF THE INVENTION

This invention relates to an improved process for purifying a natural product using a two-phase, multi-solvent system followed by back extraction and precipitation. The method allows for the removal of impurities by controlling the polarity balance of a two-phase system by manipulating the proportions of the solvents. The choice of the solvent composition allows for the product to enter and exit the process in the same solvent from which it can be isolated in a solid form. Prior processes in the isolation and purification of similar natural products required chromatography steps. This process allows for recovery of the product in the same solvent used for the extraction steps. Additionally, this method reduces the overall solvent consumption making the process economically viable for commercial use.

SUMMARY OF THE INVENTION

This invention is directed to a process for purifying a natural product after initial isolation by whole broth extraction using a two-phase, multi-solvent system after initial isolation by whole broth extraction. Recovery of the product from the back extraction step involves additional vacuum concentration and a two-stage precipitation step. Typically three or more solvents are employed since the multi-solvent system can impact the relative polarity balance of the solution in which the compound is being purified. The process of the invention can be used to purify lipophilic natural products such as echinocandin-type cyclic peptides. In particular, there is disclosed a process for purifying pneumocandin Compound I of the formula

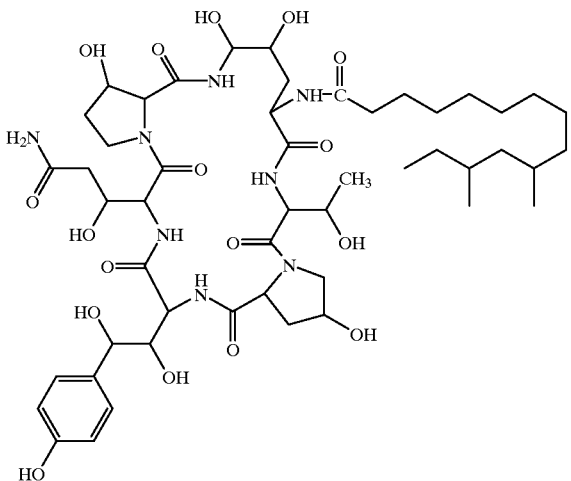

(I)

which is the starting material for the antifungal compound of the formula

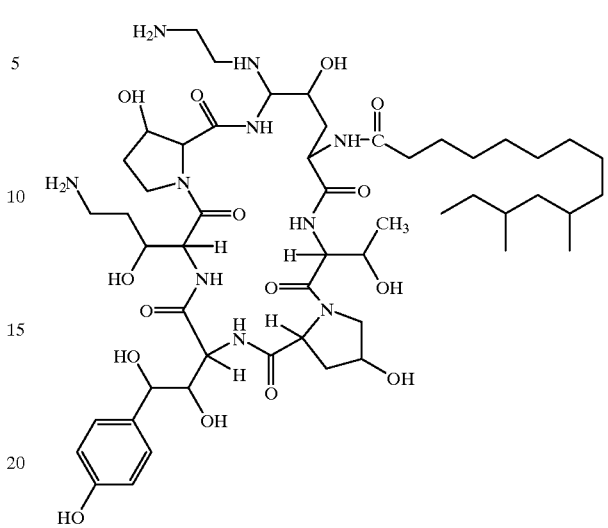

(II)

This compound has been found useful in treating fungal infections and for the treatment and prevention of infections caused by *Pneumocystis carinii*, which are often found in immunocompromised patients such as those suffering with AIDS. Compound I is disclosed and claimed in U.S. Pat. No. 5,194,377, which issued Mar. 16, 1993. Compound II is disclosed and claimed in U.S. Pat. No. 5,378,804, which issued Jan. 3, 1995.

DETAILED DESCRIPTION OF THE INVENTION

Figure 1:
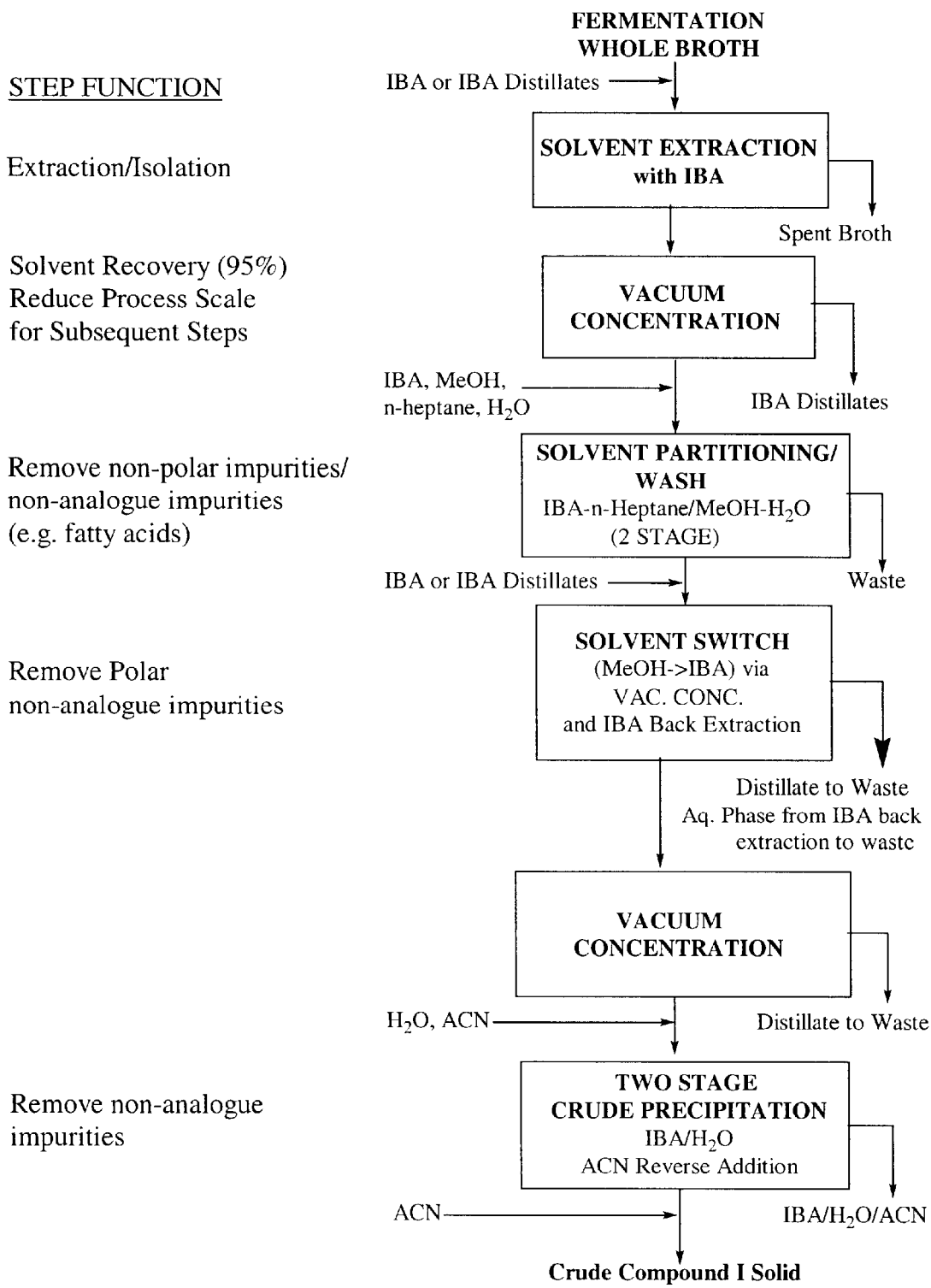
FIG. 1 is a flow chart showing the process in stepwise fashion.

This invention relates to a process for purifying a natural product comprising a) extraction of the product with a suitable solvent;

b) vacuum concentration of the extract containing the product and solvent;

c) partitioning of the solvent into a second solvent extract;

d) washing of the second solvent extract;

e) vacuum concentration of the washed second solvent extract;

f) back extracting with the first solvent;

g) vacuum concentration of the extract containing the product and the first solvent; and h) precipitation of the crude product.

In particular, there is disclosed a process for purifying a natural product derived from a fermentation or other method such as a lipopeptide such as an echinocandin using a two-phase, multi-solvent system. The process also utilizes vacuum concentration, back extraction and precipitation as the natural product goes through the purification. A crude product is defined as the desired compound and its closely related analogs.

In particular, there is disclosed a process for purifying the compound of the formula

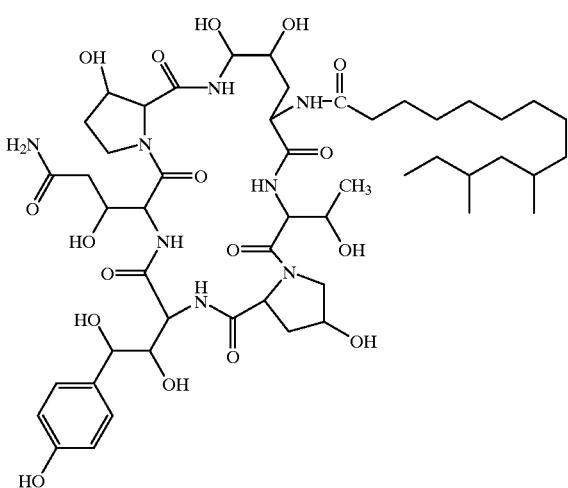

(I)

comprising
 a) extraction of Compound I with a suitable solvent;
 b) vacuum concentration of the extract containing the product and solvent;
 c) partitioning of the solvent into a second solvent extract;
 d) washing of the second solvent extract;
 e) vacuum concentration of the washed second solvent extract;
 f) back extracting with the first solvent;
 g) vacuum concentration of the extract containing the product and the first solvent; and
 h) precipitation of the crude product.

Compound I can be produced by cultivating *Glarea lozoyensis* (formerly identified as *Zalerion arboricola*) ATCC 20868 in a nutrient medium enriched in mannitol as the primary source of carbon as described in U.S. Pat. No. 5,021,341, issued Jun. 4, 1991.

The process of the invention is described relative to the purification of Compound 1. However, it is to be understood that the process can be employed to purify other natural products in the echinocandin family or other natural products utilizing the appropriate solvents.

The process of the invention involves the following steps as shown in FIG. 1. Whole broth containing Compound I at about 2.0 g/L is extracted using a water-immiscible alcohol forming a two-phase system. Alcohols useful in this step of the invention include n-propanol, n-butanol, isobutyl alcohol, sec-butanol, tert-butanol, and n-octanol. Preferably, isobutyl alcohol (IBA) is used. The two-phase system is separated producing a spent broth (lower phase) and a product bearing IBA extract (upper phase). The spent broth is removed and the concentration of Compound I is increased through vacuum distillation of the IBA extract prior to further processing. Approximately 85% of the extraction solvent, IBA, is recovered at this step.

Next, the concentrated IBA extract stream containing Compound I undergoes a two phase solvent partitioning process to remove non-polar and weakly polar non-analog impurities. This is a two-stage process utilizing the solvents as described below. During the first stage of the solvent partitioning process, Compound I is transferred from the IBA:heptane (organic) phase to the lower (aqueous) phase. The upper organic phase is discarded.

The next step for purifying Compound I is the second partitioning or wash step. The aqueous phase (containing a mixture of IBA, methanol and water) from the partitioning step, containing Compound I, is washed by addition of more IBA, heptane and water. Compound I remains in the aqueous methanol phase and the upper (IBA-heptane) phase is discarded.

Compound I is back extracted to an IBA phase utilizing a two step process involving vacuum concentration and addition of IBA and water. The aqueous phase from the wash step is vacuum concentrated to remove the majority of the methanol from the aqueous phase. During the vacuum concentration step, a two-phase system is formed; additional IBA and water are added to complete the extraction/solvent switch to the IBA phase. The upper phase, IBA back extract, contains Compound I and is composed of a solvent mixture of IBA (predominantly), methanol and water. The lower aqueous phase, containing polar impurities, is discarded.

The IBA back extract containing Compound I is again concentrated by vacuum concentration which removes the methanol and water forming an IBA/water slurry. Following this step, Compound I is precipitated via a two-stage process. The first stage involves a preliminary precipitation in an IBA/water system. The first stage precipitation is done using a dissolution/precipitation process accomplished by a controlled temperature gradient under conditions of controlled water content. A second stage precipitation involves the use of acetonitrile (ACN), an antisolvent of Compound I, to complete the precipitation step and to afford Compound I in high yield. This final two-stage precipitation step removes additional non-analog impurities. Compound I is recovered from the slurry by either filtration or centrifugation producing a wet cake. The wet cake is washed with ACN and dried under vacuum producing a crude solid containing Compound I.

The invention is described in greater detail in the following example in which all parts, preparations, ratios and percentages are by weight unless otherwise indicated.

Demonstrated Ranges

The IBA extract stream is concentrated to the target concentration of Compound I typically in an operating range of about 23 to about 53 g/L (demonstrated range from 10 to 53 g/L). In order to achieve this concentration of Compound I, the IBA extract stream is concentrated to a volume of approximately 5% of the original broth volume in order to minimize process volume and waste generation from the subsequent processing steps.

The IBA extract concentrate containing Compound I is combined in equal volumetric ratios with three other solvents, methanol, an alkane such as heptane or hexane and water. A 20% variance in charge volumes has been found to be acceptable. The ratio of the solvents is important to control the solvent polarity balance, to effect the formation of a two-phase system and to vary the ratio of the two phases. The two-phase system formed is then briefly mixed to complete the extraction. The product is then recovered in the lower phase with phase separation accomplished by means known in the art. Generally, the two-phase system is mixed under moderate shear conditions for about 5 to about 40 minutes in order to complete the extraction.

The product is typically recovered in the lower phase at high yield, greater than 95%, with about 30–40% purity. This represents an increase of about 15 to 25% in the purity from the feed, which is typically in the range of 1 about 2–18 wt %. Highly non-polar non-analogue impurities, such as oils and fatty acids are partitioned to the upper phase which contains predominantly IBA and the alkane. A portion of the IBA present in the feed partitions into the lower phase that also contains methanol and water resulting in a substantial increase in volume (typically 2 to 2.4 fold) of the phase containing Compound I. The volume increase resulting from the solvent partitioning results in a reduction in the Compound I concentration. The concentration of Compound I in the aqueous methanol extract stream is typically about 30 to about 50% of the concentration in the feed to the step. The absolute concentration of Compound I is dictated by the concentration of Compound I in the feed. The concentration of Compound I in the aqueous methanol extract is typically in the range of about 9 to about 17 g/L.

This step is then repeated to further purify the aqueous methanol extract from the first stage. Additional quantities of water, IBA and n-heptane are charged to the batch followed by mixing and separation of the two-phases. Typical additions are 0.067 volume of water, 0.25 volume of IBA and 0.25 volume of n-heptane. A 10% variance in charge volumes has been demonstrated to produce acceptable results for the step.

Unlike the first stage partitioning step, only a minor solvent partitioning occurs during the wash step. Hence, only a minor dilution of the phase containing Compound I occurs. The product stream, called washed aqueous methanol extract, typically contains Compound I in a range of about 7.4 to about 14.3 g/L, preferably about 12 g/L and 40 wt. % purity (range 32 to 45%). This is an increase of 5% purity over the feed. The yield for this second stage purification is typically greater than 80% (range 80 to 100%). The waste layer for the second stage contains impurities slightly less polar than Compound I. Solvent distribution between the two-phases in the wash step has been observed to change as a function of the impurity profile and Compound I concentration in the feed. However, the purification process is flexible enough to handle these changes without affecting purification performance. Several batches have been processed with waste layers with elevated levels of n-heptane (up to 74 vol %) with concomitant reductions in IBA, methanol and water without substantially affecting the product purity or solvent composition in the washed aqueous methanol extract phase.

The washed aqueous methanol extract from the second stage of the process is then typically vacuum concentrated 2.4 fold (range of 1.75 to 4.8 fold) to selectively remove the volatile solvents. In this case, methanol and n-heptane are removed resulting in the formation of a two-phase system. The upper phase of this system is predominantly IBA and contains about 85% of Compound I. The lower phase is predominantly aqueous. Compound I is recovered in very high yield by a back extraction using an additional portion of IBA, typically in a range of about 0.7 to 1.6 volumes, preferably 1.2 volumes. This results in an additional increase in purity. The lower aqueous phase produced contains impurities more polar than Compound I and minimal product concentration, typically less that about 200 mg/L. The back extract is then concentrated and the product recovered by means well known in the art.

EXAMPLE 1

The whole broth volume of 11355 L containing Compound I at 2.44 g/L (27.7 kg of Compound I) was charged to a 19000 L agitated tank (tank 1). Fermentation activity was terminated by contacting the whole broth with 3032 L of isobutyl alcohol for two hours producing a fixed broth stream. Recovery of Compound I was achieved using a 7600 L tank (tank 2) to complete the extraction producing an IBA extract stream. Extraction was performed using tank 2 as a controlled stirred tank (CST) reactor with a residence time in excess of two hours. The fixed broth from tank 1 and additional isobutyl alcohol were continuously fed in a controlled flowrate ratio (via mass meters) to tank 2 to achieve an overall volumetric solvent to feed ratio of 1.2 (vol IBA: vol whole broth). The IBA extract and spent broth streams produced from the extraction in tank 2 were separated using a continuous centrifuge. IBA extract was collected in a 11400 L agitated tank (tank 3) and spent broth collected for disposal in a waste tank. A total of 24.8 kg of Compound I was recovered in the IBA extract stream (12199 L @ 2.04 g/L) at a yield of 89.5% and 16.9 wt. % purity. A small amount of residual solids (2.8 v %) remained in the IBA extract stream following the continuous centrifuge step and were removed with a phase cut (following gravity settling in tank 3). The spent broth stream had a volume of 13100 L and associated Compound I concentration of 0.33 g/L at 0.4 wt. % purity.

The IBA extract (12199 L containing 24.8 kg of Compound I) was then vacuum concentrated to a final volume of 473 L in a 3800 L still (tank 4) coupled with a 7600 L receiver (tank 2). The IBA extract stream is concentrated to a volume of ~5% of the original broth volume in order to minimize process volume and waste generation in the subsequent processing steps. Processing conditions for the vacuum concentration step were 23.8±1.1 in Hg (avg.±std. dev.) and at a batch temperature of 38.9±5.7° C. (avg.±std. dev.). Upon completion of the concentration, the batch was cooled to 25° C. prior to further processing. Water was then added to 10 vol % followed by mixing for 60 minutes in tank 4 in order to redissolve Compound I that had precipitated during the vacuum concentration step. The resulting hydrated IBA extract concentrate stream had a volume of 523 L and contained 22.6 kg of Compound I at 43.1 g/L representing an overall concentration factor of 23.3 fold for the step.

The vacuum concentration of the IBA extract stream produced a distillate stream containing IBA and water that was stored in two 6800 L processing tanks. Water is preferentially removed from the stream containing Compound I during the distillation and hence the recovered distillate is two phase: a lower aqueous phase and an upper water-saturated IBA phase. The water phase was removed from the distillate by gravity settling followed by a phase cut. The resulting IBA distillate contained ~88 v % IBA and 12 v % water.

The hydrated IBA extract concentrate stream served as the feed to the next processing step—the solvent partitioning step. The hydrated IBA extract concentrate was combined with equal volumes of methanol, n-heptane and water in tank 4 in the solvent partitioning step. The contents of tank 4 were then agitated at 100 rpm for 2 minutes. Phase separation was accomplished via gravity. The subsequent phase cut was performed and the lower batch phase or aqueous methanol extract contained 23.7 kg of Compound I (1426 L @ 16.6 g/L) at 36.3 wt. % purity. The lower batch phase contained the following solvent composition: 37.9 v % water, 38.6 v % methanol, 24.3 v % IBA and 0.12 v % n-heptane. The upper (organic) waste phase contained 0.01 kg Compound I (590 L @ 0.02 g/L) at 0.02 wt. %. The upper organic phase contained the following solvent composition: 0.81 v % water, 1.9 v % methanol, 9.5 v % IBA and 87.8 v % n-heptane.

The aqueous methanol extract produced from the solvent partitioning step was subsequently washed to increase the purity of the Compound I (batch) phase. Solvent charges to the step are based on volumetric ratios to the aqueous methanol extract (Compound I phase). The wash step was performed by charging 0.067 volumes of water (96 L of which 47.6 L were from the IBA distillate charge), 0.25 volumes of IBA (405 L of IBA distillates containing 88 v % IBA and 12 v % water) and 0.25 volumes of n-heptane (370 L) to tank 4. The contents of tank 4 were then agitated and phase separation was accomplished via gravity settling.

The lower batch phase, the washed aqueous methanol extract, was cut to a 7600 L tank (tank 2) and then returned to tank 4 once the upper waste phase had been discarded. An 85 L IBA distillate rinse of tank 2 and the associated process lines was performed in the flush to ensure complete recovery of Compound I. The washed aqueous methanol extract contained 23.3 kg of Compound I (1690 L @ 13.8 g/L) at 40.6 wt. % purity. The washed aqueous methanol extract contained the following solvent composition: 35.6 v % water, 29.5 v % methanol, 33.2 v % IBA and 1.7 v % n-heptane. The upper (organic) waste phase contained 0.90 kg compound I (543 L @ 1.66 g/L) at 11.9 wt. % purity. The upper organic phase contained the following solvent composition: 03.4 v % water, 7.8 v % methanol, 35.6 v % IBA and 53.2 v % n-heptane.

The washed aqueous methanol extract from the solvent wash step (including the 85 L IBA distillate rinse) was vacuum concentrated in tank 4 (tank 2 as distillate receiver) to a volume of 795 L. The vacuum distillation required 8 hours and upon completion, the batch was cooled to 25° C. prior to the IBA back extraction step.

IBA back extraction was performed with a charge of 863 kg (1052 L) of IBA distillate to tank 4 for a back extraction ratio of 1.3 (vol IBA distillate: vol batch). Following the IBA distillate charge, the contents of tank 4 were agitated and settled prior to performing the phase cut. The back extraction produced two layers, the lower aqueous waste layer and the upper IBA extract (batch) layer. The lower waste phase was slightly amber in color. The waste phase contained 0.02 kg of Compound I (326 L @ 0.07 g/L) at 0.19 wt. % purity. The upper phase, the IBA back extract, was amber in color and slightly turbid. The IBA back extract contained 22.97 kg of Compound I (1514 L @ 15.2 g/L) at 52.8 wt. % purity.

The IBA back extract obtained following the phase cut was retained in tank 4 and vacuum concentrated to reduce batch volume. Tank 4 served as the still with tank 2 acting as the distillate receiver for the concentration. The distillation reduced the Compound I stream volume from 1514 L to a final volume of 543 L for an overall concentration factor of 2.8 fold.

At the conclusion of the vacuum concentration step, the batch was cooled to 25° C., 64 L (17 gallons) of water was added to the batch to solubilize the product, followed by 30 minutes of agitation, resulting in a final volume of 590 L. The hydrated IBA back extract partial concentrate contained 22.5 assay kg (590 L @ 38.1 g/L) and 52.1 wt. % purity.

The hydrated IBA back extract partial concentrate was further concentrated via fed-batch vacuum distillation to a volume of 195 liters. The distillation was carried out in tank 5 (400 L capacity) for 9 hours with vacuum ranging from 27 to 28.5 in Hg. vacuum, and a batch temperature of 21 to 43° C.

The concentrated IBA back extract was heated to 45° C. to re-dissolve suspended solids formed during the concentration, and 2.54 liters of DI water were added so as to bring the water content to 1.3% v/v by KF assay. The precipitation was initiated via cooling the batch from 45° C. to 20° C., at 3° C. per hour (8.3 hours total) with agitation. The precipitate slurry from tank 5 was transferred to tank 6 (760 L capacity) containing 411 liters of acetonitrile and followed by a flush of 95 liters of acetonitrile, resulting in 803 liters of acetonitrile slurry.

The majority of the acetonitrile slurry was transferred into the filter dryer (662 L capacity, 0.6 m$^2$ area) initially with the balance transferred concurrently with the filtration of the batch. The batch was pressure filtered with agitation and 1 kg/cm$^2$ nitrogen pressure for 40 minutes, until the solid filter cake appeared. This was followed by a first wash of 205 liters of acetonitrile, filtered with agitation at 1 kg/cm$^2$ nitrogen pressure for 11 minutes, and a second wash of 205 liters of acetonitrile, filtered with agitation at 1 kg/cm$^2$ nitrogen pressure for 15 minutes. The wetcake was blown with nitrogen for three hours then vacuum dried in the filter dryer at 50° C. under 25.3 in Hg vacuum with a slight nitrogen sweep for 47 hours. The resulting crude solids (31.3 kg total solids, 19.22 kg Compound I) had a purity of 61.4 wt. % and a loss on drying (L.O.D) of 2.7%. Step yield from IBA back extract partial concentrate to dried crude Compound I was 85.4%. Overall yield from fermentation broth to dried crude Compound I was 69%.

Although this process is described for Compound I, it can be used for the purification of other natural products obtained from a fermentation or other source. The keys to the invention are the ability to control the solvent polarity balance and phase ratio in the multi-solvent system. This allows for product partitioning into either the upper or lower phase and selective rejection of unwanted impurities. The particular technique employed for concentration of the extract streams can be chosen according to the specific stability requirements of the desired compound targeted for purification.

What is claimed is:

1. A process for purifying an echinocandin or a pneumocandin comprising a) extraction of a crude product comprising echinocandin or pneumocandin with a suitable solvent;

b) vacuum concentration of the extract containing the product and solvent;

c) partitioning of the solvent into a second solvent extract;

d) washing of the second solvent extract;

e) vacuum concentration of the washed second solvent extract;

f) back extracting with the first solvent;

g) vacuum concentration of the extract containing the product and the first solvent; and h) precipitation of the product from step g).

2. The process of claim 1 wherein the pneumocandin is

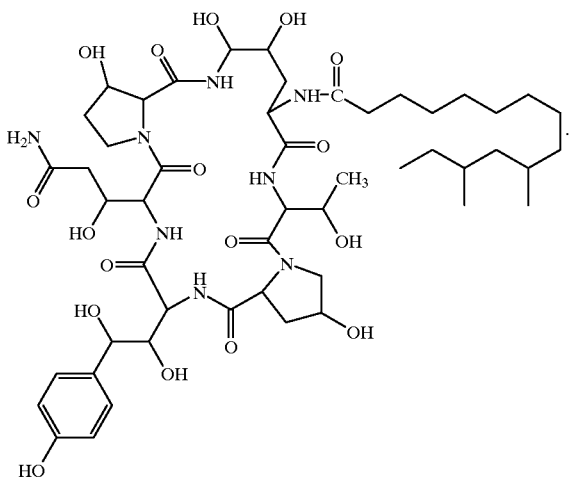

(I)

3. The process of claim 2 wherein the solvent used in the Step a) extraction is isobutyl alcohol.

4. The process of claim 2 wherein the solvents used in the solvent partitioning and wash steps of the process are selected from alkanes, alcohols and water.

5. The process of claim 4 wherein both water miscible and water immiscible alcohols are used.

6. The process of claim 5 wherein the water miscible alcohol is methanol.

7. The process of claim 5 wherein the water immiscible alcohol is selected from n-propanol, n-butanol, isobutyl alcohol, sec-butanol, tert-butanol, and n-octanol.

8. The process of claim 4 wherein the alkanes are selected from heptanes, n-heptane or hexanes.

9. The process of claim 2 wherein four solvents are employed in the solvent partition and wash steps of the purification.

10. The process of claim 9 wherein the solvents employed are water, isobutyl alcohol, n-heptane and methanol.

11. A process for purifying Compound I of the formula

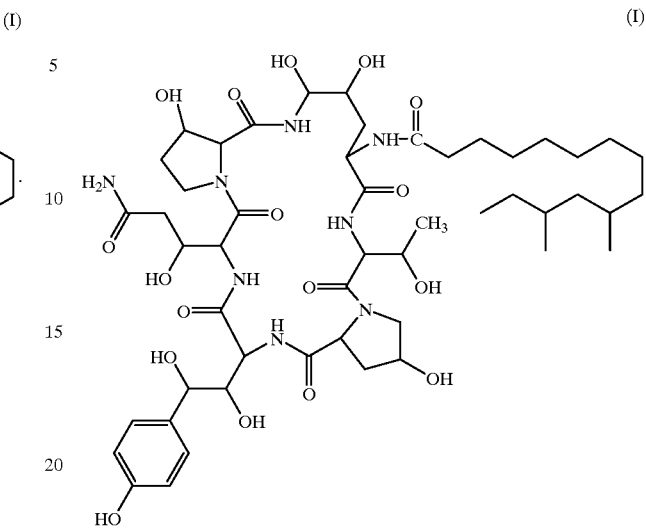

(I)

comprising
a) extraction of a crude product of Compound I with a suitable solvent;
b) vacuum concentration of the extract containing the product and solvent;
c) partitioning of the solvent into a second solvent extract;
d) washing of the second solvent extract;
e) vacuum concentration of the washed second solvent extract;
f) back extracting with the first solvent;
g) vacuum concentration of the extract containing the product and the first solvent; and
h) precipitation of the product from step g).

12. The process of claim 11 wherein the suitable solvent in the step a) extraction is a water immiscible alcohol.

13. The process of claim 12 wherein the water immiscible alcohol is isobutyl alcohol.

14. The process of claim 11 wherein the second solvent extract contains an alkane, methanol and water.

15. The process of claim 14 wherein the alkane is heptanes.

16. The process of claim 12 wherein Compound I is obtained in a range of about 49% to about 84% yield from step a) to step h) and a range from about 50% to about 64% (by weight) purity.

* * * * *